US005846727A

United States Patent [19]
Soper et al.

[11] Patent Number: 5,846,727
[45] Date of Patent: Dec. 8, 1998

[54] MICROSYSTEM FOR RAPID DNA SEQUENCING

[75] Inventors: Steven A. Soper, Baton Rouge, La.; Jack D. Davies, Mt. Vernon, Ind.; Yuli Vladimirsky, Baton Rouge, La.

[73] Assignee: Board of Supervisors of Louisiana State University and Agricultural & Mechanical College, Baton Rouge, La.

[21] Appl. No.: 865,275

[22] Filed: May 29, 1997

[51] Int. Cl.$^6$ .............................. C12M 1/00; C12M 3/04; C12N 15/00; C07H 21/00

[52] U.S. Cl. .................................. 435/6; 935/77; 935/78; 536/25.32; 204/451; 204/601; 435/285.2; 435/287.2

[58] Field of Search .................................. 435/6, 5, 91.1, 435/91.2, 188, 187.2; 204/451, 600; 216/2, 41, 42, 44, 48, 51; 356/346, 319; 536/23.1, 26.6, 24.3; 436/546; 209/577; 530/388.1

[56] References Cited

U.S. PATENT DOCUMENTS

| 5,230,781 | 7/1993 | Middendorf et al. ................. 204/182.8 |
| 5,360,523 | 11/1994 | Middendorf et al. ................. 204/182.8 |
| 5,366,603 | 11/1994 | Middendorf et al. ................. 204/182.8 |
| 5,374,527 | 12/1994 | Grossman ..................................... 435/6 |
| 5,405,746 | 4/1995 | Uhlen ............................................ 435/6 |
| 5,484,701 | 1/1996 | Cocuzza et al. ............................. 435/6 |

FOREIGN PATENT DOCUMENTS

0708331A1  4/1996  European Pat. Off. .

OTHER PUBLICATIONS

Y. Xia, Soft Lithography: Micro– and Nanofabrication Based on Microcontact Printing and Teplica Molding, *Engineeriing Materials Science, Diss. Abs.* vol. 57, p. 6507–B (1997).
L. Amankwa et al., "Trypsin–Modified Fused–Silica Capillary Microreactor for Peptide Mapping by Capillary Zone Electrophoresis," *Anal. Chem.*, vol. 64, pp. 1610–1613 (1992).
L. Amankwa et al., "On–Line Peptide Mapping by Capillary Zone Electrophoresis," *Anal. Chem.*, vol. 65, pp. 2693–2697 (1993).
C. Effenhauser et al., "High–Speed Separation of Antisense Oligonucleotides on a Micromachined Capillary Electrophoresis Device," *Anal. Chem.*, vol. 66, pp. 2949–2593 (1994).
Effenhauser et al., "Manipulation of Sample Fractions on a Capillary Electrophoresis Chip," *Anal. Chem.*, vol. 67, pp. 2284–2287 (1995).
A. Wooley et al., "Ultra–High–Speed DNA Sequencing Using Capillary Electrophoresis Chips," *Anal. Chem.*, vol. 67, pp. 3676–3680 (1995).
S. Jacobson et al., "Integrated Microdevice for DNA Restriction Fragment Analysis," *Anal. Chem.*, vol. 68, pp. 720–723 (1996).
Z. Liang et al., "Microfabrication of a Panar Absorbance and Flourescence Cell for Integrated Capillary Electrophoresis Devices," *Anal. Chem.*, vol. 68, pp. 1040–1046 (1996).

S. Hjertén "High–Performance Electrophoresis Elimination of Electroendosmosis and Solute Adsorption," *J. Chromatogr.*, vol. 347, pp. 191–198 (1985).
A. Cohen et al., "Separation and Analysis of DNA Sequence Reaction Products by Capillary Gel Electrophoresis," *J. Chromatogr.*, vol. 516, pp. 49–60 (1990).
S. Stahl et al., "Solid Phase DNA Sequencing Using the Biotin–Avidin System,"*Nucl. Acid Res.*, vol. 16, pp. 3025–3037 (1988).
T. Hawkins et al., "DNA Purification and Isolation Using a Solid Phase," *Nucl. Acid Res.*, vol. 22, pp. 4543–4544 (1994).
S. Huang et al., "Binding of Biotinylated DNA to Strepavidin–Coated Polystyrene Latex," *Anal. Biochem.*, vol. 222, pp. 441–449 (1994).
A. Rolfs et al., "Fully–Automated, Nonradioactive Solid–Phase Sequencing of Genomic DNA Obtained from PCR," *Biotechniques*, vol. 17, pp. 782–787 (1994).
T. Hultman et al., "Direct Solid Phase Sequencing of Genomic and Plasmid DNA Using Magnetic Beads as Solid Supports," *Nucl. Acid Res.*, vol. 17, pp. 4937–4945 (1989).
M. Uhlen et al., "Magnetic Separation of DNA," *Nature*, vol. 340, pp. 733–734 (1989).

(List continued on next page.)

*Primary Examiner*—Lisa B. Arthur
*Assistant Examiner*—Jehhanne Souaya
*Attorney, Agent, or Firm*—John H. Runels

[57] ABSTRACT

A system is disclosed for the rapid and cost-effective sequencing of DNA. There are three principal components of the system: (1) a microreactor, which prepares DNA sequencing "ladders" using solid-phase techniques, preferably in capillary tubes whose volumes are on the order of 10–1000 nanoliters, preferably 10–200 nanoliters; (2) a microfabricated electrophoresis capillary separation unit; and (3) a fluorescence detector with single-mode optical fibers interfaced directly to the electrophoresis capillary. The system is suitable for a highly multiplexed, automated DNA sequencing device Typical. steps in sequencing are as follows: (1) PCR amplification of a DNA template in microtiter dishes using labelled primers, e.g., primers labelled with biotin; (2) immobilizing the labelled PCR products on the walls of one or more capillary tubes having volumes on the order of 10–200 nanoliters; (3) preparing nanoliter quantities of labelled Sanger extension products of the amplified DNA; (4) purifying the oligonucleotide sequencing ladders; (5) high speed electrophoretic separation of the sequencing ladders; and (6) near-infrared, laser-induced fluorescence detection of the oligonucleotides. Base-calling is preferably performed in a single lane format with a single fluorophore, in which the bases are distinguished by different fluorescence lifetimes of dyes that otherwise have similar absorption and fluorescence emission spectra at the wavelengths used. Typical read lengths are on the order of 400–500 bases. Fluorescence is performed on-chip with one single-mode optical fiber carrying the excitation light to the capillary channel, and a second single-mode optical fiber collecting the fluorescent photons. Only sub-microliter volumes of expensive sequencing reagents and dye-labeled ddNTPs are required in this system.

39 Claims, 2 Drawing Sheets

OTHER PUBLICATIONS

D. Williams et al., "Single–Lane, Single–Fluor Sequencing using Dideoxy–Labled, Heavy–Atom Modified Near–IR Fluorescent Dyes," *SPIE,* vol. 2386, pp. 55–56 (proceedings paper, presentation in San Jose, California, Feb. 6, 1995).

D. Harrison et al., "Capillary Electrophoresis and Sample Injection Systems Integrated on a Planar Glass Chip," *Anal. Chem.,* vol. 64, pp. 1926–1932 (1992).

Z. Fan et al., "Micromachining of Capillary Electrophoresis Injectors and Separators on Glass Chips and Evaluation of Flow at Capillary Intersections," *Anal. Chem.,* vol. 66, pp. 177–184 (1994).

S. Jacobson et al., "Effects of Injection Schemes and Column Geometry on the Performance of Microchip Electrophoresis Devices," *Anal. Chem.,* vol. 66, pp. 1107–1113 (1994).

S. Soper et al., "Micro–DNA Sequence Analysis Using Capillary Electrophoresis and Near–IR Fluorescence Detection," *SPIE,* vol. 2680, pp. 235–246 (proceedings paper, San Jose, California, Feb. 2, 1996).

D. Williams, slides presented at two meetings (Orlando, Florida, Jan. 24, 1996; and Baton Rouge, Louisiana, Mar. 16, 1996).

S. Soper et al., "On–Line Fluorescence Lifetime Determinations in Capillary Electrophoresis," poster (Orlando, Florida, Jan. 24, 1996).

S. Soper et al., "On–Line Fluorescence Lifetime Determinations in Capillary Electrophoresis," *Anal. Chem.,* vol. 67, pp. 4358–4365 (Dec. 1, 1995).

D. Williams et al., "Ultrasensitive Near–IR Fluorescence Detection for Capillary Gel Electrophoresis and DNA Sequencing Applications," *Anal. Chem.,* vol. 67, pp. 3427–3432 (Oct. 1, 1995).

S. Soper et al., "Multiplexed DNA Sequencing Using CGE and NIR Fluorescence," LSU Grant Application No. 5688, submitted to the Department of Health and Human Services, Public Health Service May 24, 1994.

S. Soper et al., "High Throughput DNA Sequencing Using Micro–Reactors and Micro–CE,"LSU Grant Application, submitted to the Department of Health and Human Services, Public Health Service, Aug. 22, 1995.

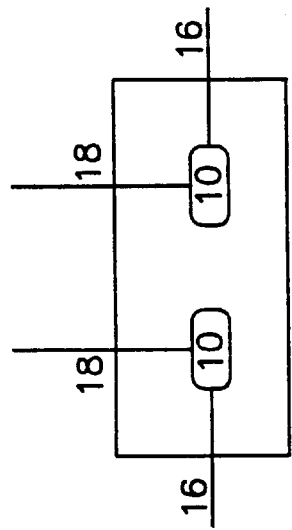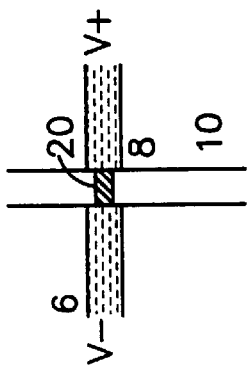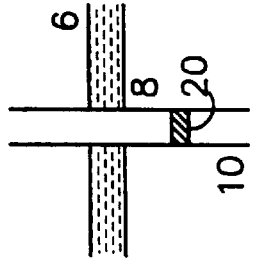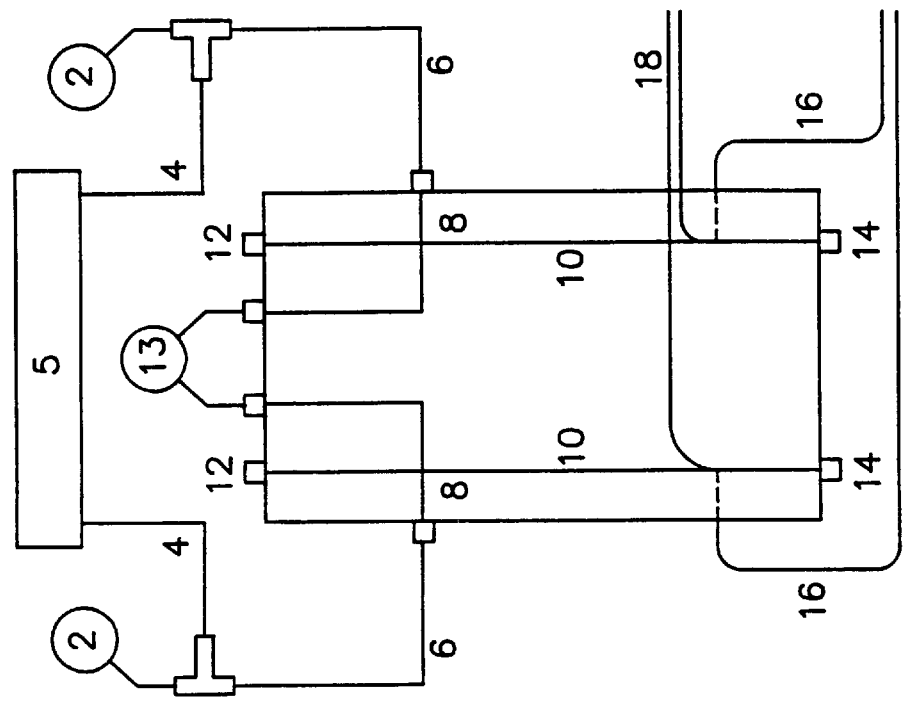

MICROSYSTEM FOR RAPID DNA SEQUENCING

The development of this invention was partially funded by the Government under grants HG 00824-02 and HG 01499-01 awarded by the National Institutes of Health. The Government has certain rights in this invention.

This application is a continuation of Provisional application Ser. No. 60/077,187 filed Jun. 6, 1996.

This invention pertains to novel systems for sequencing DNA molecules, particularly to micro-systems adapted for sequencing DNA molecules rapidly with low consumption of reagents.

There is a continuing need for faster, less expensive systems to sequence deoxyribonucleic acid ("DNA"). Such systems are needed, for example, in the ongoing Human Genome Project, whose eventual goal is to completely sequence the 3 billion DNA base pairs that make up the genetic blueprint of a human being; as well as to completely sequence the genomes of several other model organisms such as *Saccharomyces cerevisiae, Caenorhabditis elegans,* and *Drosophila melanogaster.* To meet the goals of the Human Genome Project, faster, more economical methods for sequencing DNA will be needed than are currently available.

U.S. Pat. No. 5,374,527 discloses the use of a low viscosity medium in capillary electrophoretic sequencing of DNA, namely a solution containing between about 4 and about 7 weight percent linear polyacrylamide ("LPA") molecules. Detection was preferably performed by detection of fluorescent labels.

U.S. Pat. No. 5,405,746 discloses a method of sequencing DNA in which the terminus of one strand of a double-stranded DNA molecule is immobilized on a solid support, for example with a biotin-avidin system; the complementary DNA strands are separated; the unbound strand is removed; and fluorescent- or isotope-labeled Sanger extension products are prepared on the bound single-stranded DNA molecules. One method for preparing the immobilized single-stranded DNA was by PCR amplification using primers with means such as biotin for attaching oligonucleotides, to produce directly immobilized single-stranded DNA prior to preparing Sanger extension products. The biotinylated DNA was immobilized on an avidin-agarose gel in a conventional slab format. Detection followed electrophoresis of radiolabelled reaction products.

U.S Pat. No. 5,484,701 discloses a process for isolating extension products of PCR amplification, in which biotinylated primers are used in the PCR amplification to produce biotinylated extension products; the extension products are immobilized by reaction with a biotinbinding protein such as avidin or streptavidin; the immobilized products are separated from the liquid phase of the reaction; and the immobilized complex is denatured with formamide. Sanger extension products were sequenced by electrophoresis of radiolabelled or fluorescent products on a gel, presumably a conventional slab gel.

U.S Pat. Nos. 5,230,781 and 5,366,603 each disclose systems for sequencing DNA by electrophoresis on conventional slab gels, using infrared or near-infrared dyes to label the bases, with a laser diode to provide the excitation frequency, and an avalanche photodiode detector.

U.S Pat. No. 5,360,523 discloses a system for sequencing DNA by electrophoresis on conventional gel slabs or in gel-filled or buffer-filled capillary tubes, using infrared or near-infrared dyes to label the bases, with a laser diode to provide the excitation frequency, and an automated scanning microscope for detection.

L. Amankwa et al., "Trypsin-Modified Fused-Silica Capillary Microreactor for Peptide Mapping by Capillary Zone Electrophoresis," *Anal. Chem.,* vol. 64, pp. 1610–1613 (1992) discloses a system in which trypsin, immobilized via a biotin-avidin-biotin coupling to the inner surface of a capillary, was used to digest minute amounts of protein. Capillary zone electrophoresis was used to separate the tryptic peptides in the resulting digest. The labeled peptides were then detected with laser-induced fluorescence. In a subsequent paper, L. Amankwa et al., "On-Line Peptide Mapping by Capillary Zone Electrophoresis," *Anal. Chem.,* vol. 65, pp. 2693–2697 (1993) discloses coupling this enzyme-modified capillary reactor to an on-line capillary for separation of the tryptic peptides by capillary zone electrophoresis.

C. Effenhauser et al., "High-Speed Separation of Antisense Oligonucleotides on a Micromachined Capillary Electrophoresis Device," *Anal. Chem.,* vol. 66, pp. 2949–2953 (1994) discloses the rapid capillary electrophoretic separation of single-stranded oligonucleotides 10–25 bases in length. The separation was performed on a micromachined glass plate. Pipet tips glued to holes in a cover plate served as reservoirs for the oligonucleotides. Detection was performed by laser-induced fluorescence at visible wavelengths. Extension of the technique to DNA sequencing was mentioned as a possibility, although it was uncertain whether oligonucleotides in the relevant size range could be resolved.

C. Effenhauser et al., "Manipulation of Sample Fractions on a Capillary Electrophoresis Chip," *Anal. Chem.,* vol. 67, pp. 2284–2287 (1995) discloses the withdrawal of selected sample zones following capillary electrophoresis by switching electrical potentials applied to a channel system etched into a glass plate.

A. Woolley et al., "Ultra-High-Speed DNA Sequencing Using Capillary Electrophoresis Chips," *Anal. Chem.,* vol. 67, pp. 3676–3680 (1995) discloses sequencing DNA by capillary electrophoresis in polymer-coated capillary channels microfabricated on a glass chip. Detection was performed by laser-induced fluorescence at visible wavelengths.

S. Jacobson et al., "Integrated Microdevice for DNA Restriction Fragment Analysis," *Anal. Chem.,* vol. 68, pp. 720–723 (1996) discloses a microdevice for performing restriction digesting and electrophoretic sizing sequentially on-chip, in channels wet-etched in glass and coated with polymer to minimize electroosmotic flow.

Z. Liang et al., "Microfabrication of a Planar Absorbance and Fluorescence Cell for Integrated Capillary Electrophoresis Devices," *Anal. Chem.,* vol. 68, pp. 1040–1046 (1996) discloses a microfabricated absorbance and fluorescence detection cell for capillary electrophoresis on a U-cell etched onto a glass substrate, using single-mode and multi-mode optic fibers.

S. Hjertén, "High-Performance Electrophoresis Elimination of Electroendosmosis and Solute Adsorption," *J. Chromatogr.,* vol. 347, pp. 191–198 (1985) discloses that electroendosmosis and adsorption of solute onto capillary walls during capillary electrophoresis due to charges on the inner surface of a glass capillary could be decreased by coating the capillary with a mono-molecular layer of non-cross-linked polyacrylamide.

A. Cohen et al., "Separation and Analysis of DNA Sequence Reaction Products by Capillary Gel Electrophoresis," *J. Chromatogr.,* vol. 516, pp. 49–60 (1990) discloses the use of capillary gel electrophoresis to separate DNA sequencing reaction products, with detection performed by laser-induced fluorescence. The capillary columns were treated with methacryloxypropyltrimethoxysilane before the gel was introduced.

S. Stahl et al., "Solid Phase DNA Sequencing Using the Biotin-Avidin System," *Nucl. Acid Res.*, vol. 16, pp. 3025–3037 (1988) discloses binding biotin-linked DNA to an avidin-agarose gel, where the immobilized DNA was used to prepare dideoxy oligonucleotide sequencing ladders.

T. Hawkins et al., "DNA Purification and Isolation Using a Solid Phase," *Nucl. Acid Res.*, vol. 22, pp. 4543–4544 (1994) discloses the immobilization of DNA on carboxyl coated magnetic particles in the presence of high concentrations of polyethylene glycol and sodium chloride.

S. Huang et al., "Binding of Biotinylated DNA to Streptavidin-Coated Polystyrene Latex," *Anal. Biochem.*, vol. 222, pp. 441–449 (1994) discloses binding biotin-linked DNA to magnetic particles coated with streptavidin, and also to polystyrene latex particles coated with streptavidin.

A. Rolfs et al., "Fully-Automated, Nonradioactive Solid-Phase Sequencing of Genomic DNA Obtained from PCR," *BioTechniques*, vol. 17, pp. 782–787 (1994) discloses binding biotin-linked DNA to paramagnetic particles coated with streptavidin in the solid-state preparation of purified Sanger dideoxy sequencing ladders with fluorescent dye labelled primers.

T. Hultman et al., "Direct Solid Phase Sequencing of Genomic and Plasmid DNA Using Magnetic Beads as Solid Supports," *Nucl. Acid Res.*, vol. 17, pp. 4937–4945 (1989) discloses binding biotin-linked DNA to magnetic beads coated with streptavidin in the solid-state preparation of purified Sanger dideoxy sequencing ladders using both radiolabels and fluorescent labels.

M. Uhlen et al., "Magnetic Separation of DNA," *Nature*, vol. 340, pp. 733–734 (1989) discloses a biotin-streptavidin system for immobilizing DNA on magnetic beads for amplification and sequencing reactions, as well as other applications for magnetic beads.

D. Williams et al., "Single-Lane, Single-Fluor Sequencing using Dideoxy-Labeled, Heavy-Atom Modified Near-IR Fluorescent Dyes," *SPIE*, vol. 2386, pp. 55–65 (proceedings paper, presentation in San Jose, Calif., Feb. 6, 1995) discloses the use of capillary gel electrophoresis in DNA sequencing, in a polymer-coated silica capillary, with detection by near-infrared fluorescence. The different ddNTP's were labeled with the same dye, with molar concentrations varying in a ratio of 4:2:1:0; the bases were then distinguished from one another by fluorescence intensity measurements. Also disclosed is the alternative method of base-calling by measuring fluorescence lifetimes of certain heavy-atom-modified, near-infrared dyes, with similar absorption and emission spectra, but different fluorescence lifetimes.

D. Harrison et al., "Capillary Electrophoresis and Sample Injection Systems Integrated on a Planar Glass Chip," *Anal. Chem.*, vol. 64, pp. 1926–1932 (1992) discloses the micromachining of a manifold of capillary electrophoresis columns on a glass chip, with valveless switching of fluid flow between capillaries achieved by the application of electrical voltages to create electroosmotic pumping.

Z. Fan et al., "Micromachining of Capillary Electrophoresis Injectors and Separators on Glass Chips and Evaluation of Flow at Capillary Intersections," *Anal. Chem.*, vol. 66, pp. 177–184 (1994) discloses a capillary electrophoresis system on a glass chip with an integrated sample injector, in which fluid flow was controlled by the application of electric potentials.

S. Jacobson et al., "Effects of Injection Schemes and Column Geometry on the Performance of Microchip Electrophoresis Devices," *Anal. Chem.*, vol. 66, pp. 1107–1113 (1994) discloses a capillary electrophoresis device on a glass chip in which the injection volume was said to be accurately controllable.

Being disclosed to the Patent and Trademark Office to fulfill applicants' duty of candor, but believed not to be prior art, are the following papers, conference proceedings, or poster presentations that disclose, in pertinent part, the inventors' own work: S. Soper et al., "Micro-DNA Sequence Analysis Using Capillary Electrophoresis and Near-IR Fluorescence Detection," *SPIE*, vol. 2680, pp. 235–246 (proceedings paper, San Jose, Calif., Feb. 2, 1996); D. Williams, slides presented at two meetings (Orlando, Fla., Jan. 24, 1996; and Baton Rouge, La., Mar. 16, 1996); S. Soper et al., "On-Line Fluorescence Lifetime Determinations in Capillary Electrophoresis," poster (Orlando, Fla., Jan. 24, 1996); S. Soper et al., "On-Line Fluorescence Lifetime Determinations in Capillary Electrophoresis," *Anal. Chem.*, vol. 67, pp. 4358–4365 (Dec. 1, 1995); and D. Williams et al., "Ultrasensitive Near-IR Fluorescence Detection for Capillary Gel Electrophoresis and DNA Sequencing Applications," *Anal. Chem.*, vol. 67, pp. 3427–3432 (Oct. 1, 1995).

Also being disclosed to the Patent and Trademark Office to fulfill applicants' duty of candor, but believed not to be prior art, are the following two grant applications: S. Soper et al., "Multiplexed DNA Sequencing Using CGE and NIR Fluorescence," LSU Grant Application No. 5688, submitted to the Department of Health and Human Services, Public Health Service May 24, 1994 (although the abstract of this application was published approximately one year after the application was submitted); and S. Soper et al., "High Throughput DNA Sequencing Using Micro-Reactors and Micro-CE," LSU Grant Application, submitted to the Department of Health and Human Services, Public Health Service, Aug. 22, 1995.

Prior microfabricated sequencing devices have not achieved the level of integration, and therefore efficiency, reported here. Prior microfabricated electrophoresis devices have used a glass substrate and wet-etching chemical techniques. There are several difficulties with these prior systems: (1) Because a glass substrate has been used, and because glass has considerable surface charge, a polymeric coating has been required for analyzing DNA samples. After several runs, the polymer coating degrades in the high electric fields used in electrophoresis, rendering the device useless. (2) Wet etching techniques produce features having low contrast, and having poorly-defined channels. (3) Wet etching precludes the use of integrated three-dimensional structures such as detection optics. (4) Sample delivery has been limited by micropipet tips permanently sealed to the device and filled with DNA sample. Such delivery limits the device to use with a single sample, and requires chip replacement for subsequent analyses. (5) Sequencing ladders have been prepared in volumes much larger than the volumes used in separation and detection, effectively wasting large amounts of reagent.

The Novel System

A novel system has been discovered for the rapid and cost-effective sequencing of DNA. There are three principal components of the novel system: (1) a microreactor, which prepares DNA sequencing "ladders" using solid-phase techniques, preferably in capillary tubes whose volumes are on the order of 10–1000 nanoliters, preferably not more than about 200 nanoliters; (2) a microfabricated electrophoresis capillary separation unit, which separates the components of the sequencing ladders by size; and (3) a fluorescence detector with single-mode optical fibers interfaced directly to the electrophoresis capillary, for detecting and identifying the bases separated in the capillary.

The invention is suitable for a highly multiplexed, automated DNA sequencing device. Typical steps in sequencing are as follows: (1) PCR amplification of a DNA template in microtiter dishes using labelled primers, e.g., primers labelled with biotin; (2) immobilizing the labelled PCR products on the walls of one or more capillary tubes having volumes preferably on the order of 10–200 nanoliters; (3) preparing nanoliter quantities of labelled Sanger extension products of the amplified DNA; (4) purifying the oligonucleotide sequencing ladders; (5) high speed electrophoretic separation of the sequencing ladders; and (6) near-infrared, laser-induced fluorescence detection of the oligonucleotides. Base-calling is preferably performed in a single lane format with a single fluorophore, in which the bases are distinguished by different fluorescence lifetimes of dyes that otherwise have similar absorption and fluorescence emission spectra at the wavelengths used.

The device accepts DNA templates amplified, for example, by PCR in 96-well microtiter plates using a biotinylated primer. The resulting double-stranded, biotinylated PCR templates are immobilized onto the walls of fused-silica capillary tubes whose volumes are preferably on the order of 10–200 nL. These capillary tubes have previously been modified with avidin (or alternatively streptavidin), which serves as an anchor to immobilize the biotin-linked double-stranded DNA's. The DNA oligonucleotides are then purified and denatured, and dye-labelled Sanger dideoxy products are produced directly in the tube using solid-surface methods. The Sanger products are then decoupled from the avidin, and are injected directly into a multiplexed capillary electrophoresis ("CE") system for fast separations of the Sanger products by size. Typical read lengths are on the order of 400–500 bases. Fluorescence is performed on-chip with one single-mode optical fiber carrying the excitation light to the capillary channel, and a second single-mode optical fiber collecting the fluorescent photons.

Advantages of the novel system include the use of sub-microliter volumes of expensive sequencing reagents and dye-labeled ddNTPs; the ability to automate the procedures for purifying PCR products, preparing sequencing ladders, and injecting the sequencing ladders into the CE array; the ability to perform high speed separations in the CE array; and the use of a highly efficient base-calling scheme using a single lane, single-dye format.

A major advantage of the novel capillary reactor is the significant reduction in reagent costs due to the substantial reduction in sample volumes. A conventional sequencing protocol using the standard Sequenase™ kit for preparing sequencing ladders and dye-labeled ddNTP's for $3 \times 10^9$ bases of raw sequencing information (assuming no redundancy), would cost approximately $87,000,000 for reagents alone. By reducing the reactor volume in accordance with the present invention, the reagent costs are reduced by a factor of about 110, to about $790,000.

In prior applications, even where sample volumes on the order of 10–500 pL have been used for electrophoresis and detection, the sequencing reactions have typically been conducted on a $\mu$L scale, leading to much "wasted" reagent, especially significant in a project whose scale is as large as that of the Human Genome Project. In accordance with the present invention it is possible to prepare reaction products on a scale commensurate with the needs of the separation technology used, reducing the amounts of reagent required.

The components of the novel system may readily be integrated to allow sample preparation, separation, and detection to be carried out in about 15–20 minutes, approximately 5 times faster than is possible with existing systems, using a device that is no bigger than a shoe box.

Other advantages of the novel system include the following: the components of the device may be reused many times before replacement is necessary; detection is performed with integrated fiber optic components that do not need to be re-aligned between cycles; and the components may readily be integrated into a multiplexed device capable of very high throughput with minimal "down time." The integrated instrument prepares sequencing ladders, inserts the ladders directly onto the separation device, fractionates the oligonucleotides in as little as 15 minutes, and detects them with high sensitivity. This system is well-suited for applications other than sequencing, such as forensic uses and genetic mapping.

At 10–15 minutes per cycle, and 400 bases per cycle per lane, and 24 independent electrophoresis lanes total, about 1,000,000 bases may be sequenced per day with a single device. Rather than increase the number of individual lanes indefinitely, which would increase the complexity of maintenance and upkeep, it is preferred to maximize the efficiency of the individual lanes, using no more than 24 lanes per device. Upkeep and maintenance for a given device are thus reduced. Operational upkeep is considerably simpler than would be the case for a device having hundreds of lanes running in parallel.

BRIEF DESCRIPTION OF THE DRAWINGS

FIG. 1($a$) depicts an embodiment of a micro-capillary electrophoresis system in accordance with the present invention.

FIG. 1($b$) depicts a cross-sectional view of the on-chip detection region of this system.

FIGS. 1($c$) and 1($d$) depict an expanded view of an injection T in this system, showing first the loading and then the electrokinetic injection of a DNA sample plug.

THE REACTION CAPILLARIES

Figure 3:
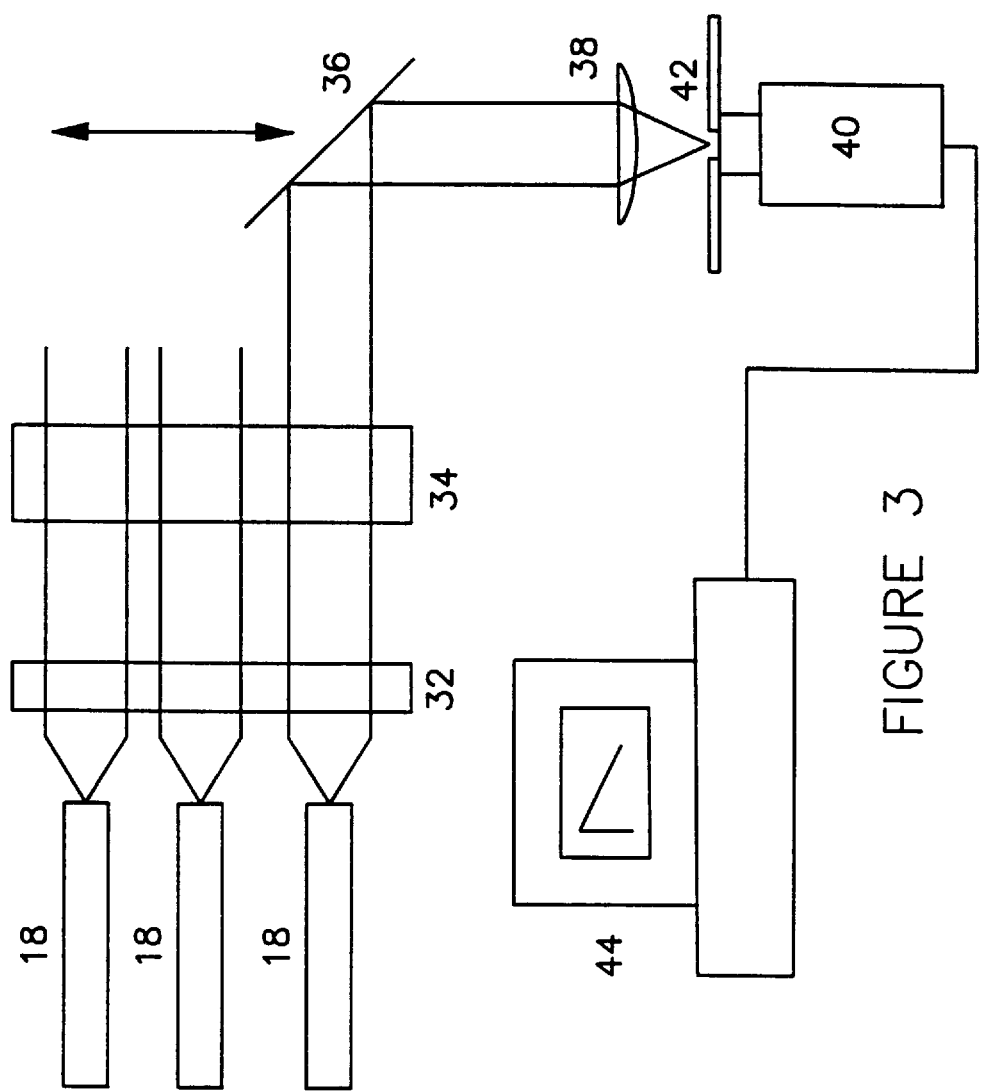
FIG. 3 depicts an optical system for collecting and processing the fluorescence signals from the collection fibers.

Sample Amplification and Purification. DNA templates to be sequenced may be amplified, for example, by multiplexed polymerase chain reactions ("PCR") on a microtiter scale. See, e.g., A. Rosenthal et al., "Large-Scale Production of DNA Sequencing Templates by Microtiter Format PCR," *Nucl. Acid Res.*, vol. 21, pp. 173–174 (1993). Templates may, for example, be amplified by PCR in conventional 96-well microtiter dishes, from which the templates may be delivered to the microreactors robotically. One of the flanking PCR primers is biotinylated at the 5' position by covalent attachment with a 5–6 carbon linker (e.g., (—CH$_2$—)$_5$). After the templates are amplified, they are purified so that excess dNTP's, enzymes, truncated products, and salts are removed prior to preparing sequencing ladders. The purification process may, for example, use known solid phase methods for biotin-containing PCR products linked to surface-immobilized avidin molecules. These methods may be used to clean PCR products to prepare them for sequencing and, if desired, also to prepare the sequencing ladders directly on the solid surface. See, e.g., S. Stahl et al., "Solid Phase DNA Sequencing Using the Biotin-Avidin System,"

Nucl. Acid Res., vol. 16, pp. 3025–3037 (1988); T. Hultman et al., "Direct Solid Phase Sequencing of Genomic and Plasmid DNA Using Magnetic Beads as Solid Supports," Nucl. Acid Res., vol. 17, pp. 4937 ff (1989); M. Uhlen, "Magnetic Separation of DNA," Nature, vol. 340, pp. 733–734 (1989); S. Huang et al., "Binding of Biotinylated DNA to Streptavidin-Coated Polystyrene Latex," Anal. Biochem., vol. 222, pp. 441–449 (1994); A. Rolfs et al., "Fully-Automated, Nonradioactive Solid-Phase Sequencing of Genomic DNA Obtained from PCR," BioTechniques, vol. 17, pp. 782–787 (1994); and T. Hawkins etal., "DNA Purification and Isolation Using a Solid Phase," Nucl. Acid Res., vol. 22, pp. 4543–4544 (1994).

The advantages of solid surface purification and sequencing include the ease of automation; high-yield, reproducible reactions; and the need for small amounts of reagents. A solid substrate that is commonly used in molecular biology protocols is a magnetic bead coated with avidin. However, magnetic beads can be quite expensive, especially when performing many reactions in a large-scale sequencing project.

The biotin-avidin system, while preferred, may be replaced with another high affinity complex system, for example an antigen/monoclonal antibody system. The two components of such a "high affinity complex" system should have a strong and selective affinity for binding one another non-covalently (at least about $K=10^8$ L/mol, more preferably at least about $10^{10}$ L/mol).

Sample Immobilization. A preferred immobilization technique is to immobilize avidin onto the wall of a microcapillary tube. The chemistry used for this immobilization may be that, for example, of L. Amankwa et al., "Trypsin-Modified Fused-Silica Capillary Microreactor for Peptide Mapping by Capillary Zone Electrophoresis," Anal. Chem., vol. 64, 1610–1613 (1992); and L. Amankwa et al., "On-Line Peptide Mapping by Capilary Zone Electrophoresis," Anal. Chem., vol. 65, pp. 2693–2697 (1993).

A preferred reaction capillary for attaching a double-stranded PCR-biotinylated template comprises a 25–50 μm i.d. fused-silica column approximately 10 cm in length, with a total volume of about 50–200 nL. The small volume of the reaction capillary minimizes the volume of sequencing and wash reagents required, significantly reducing the costs associated with performing repeated sequencing reactions. An additional advantage is that the thin wall of a capillary and its high surface-to-volume ratio permit rapid thermal equilibration, reducing temperature transition times.

The capillary is prepared by treating it with (3-aminopropyl)trimethoxysilane (3-ATPS) and, after a 30 min incubation period, air-drying and subsequently treating with sulfosuccinimidyl-6-(biotinamido)hexanoate (NHS-LC-biotin). Avidin suspended in phosphate buffer (pH=7.4) is added to the column, where it binds to the surface-immobilized biotin molecules. The schematic structure of such an avidin-modified capillary wall bound to a biotin-linked PCR template is as follows:

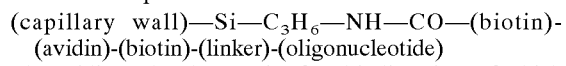

The avidin molecule contains four binding sites, of which two are used. (The remaining two potential binding sites are sterically inaccessible.) The advantage of covalently attaching biotinto the capillary wall rather than attaching avidin directly to the wall is that this procedure simplifies regeneration and reuse of the capillary. If avidin were directly bound to the capillary wall, then after a biotinylated template had bound to the surface it would be difficult to subsequently remove the template from the reaction capillary for analysis without also denaturing the avidin protein, due to the strong association constant between these species ($K_b=10^{15}$ $M^{-1}$). Regenerating the reaction capillary once the avidin was denatured would be difficult. By contrast, using the biotin-avidin-biotin structure allows the biotinylated PCR template to be removed from the column without denaturing the column. For example, treating the capillary with either phenol or a formamide solution at 65°–90° C. denatures the avidin molecules without disturbing the biotin molecules. After removing the PCR templates, the biotin-linked column can then be regenerated by reaction with a fresh solution of avidin. Thus the reaction capillary may be reused after a simple regeneration step.

The double-stranded PCR template is immobilized onto the surface of the biotin-avidin-coated capillary from a standard binding buffer of TRIS-HCl, EDTA, and either NaCl or LiCl (1–3 M) to improve binding. After a 5–10 min incubation period, the immobilized templates are washed with a flowing buffer stream to remove any excess reagents or by-products from the PCR reaction.

Sequencing Ladders. Sequencing is preferably performed using the Sanger dideoxy method. Alternative methods of preparing sequencing ladders, such as the Maxam-Gilbert method, could also be used. Sequencing ladders are prepared using Sanger chain terminating methods generally known in the art, using a low concentration of dye-labeled dideoxynucleotide triphosphates ("ddNTP's"). The sequencing ladders are prepared directly in the reaction capillary using the immobilized PCR products, with standard solid-surface sequencing chemistries, albeit on a smaller scale than has previously been done. This system is suitable for use with any DNA polymerase, with preference given to copy fidelity. The currently preferred polymerase is T7 DNA polymerase.

Advantages of performing the sequencing reactions within the reaction capillary include the following: sample handling is minimized; the reactions may be performed in nL volumes, reducing the amounts of reagents required; the procedures are readily automated; and after denaturing, the immobilized single stranded DNA can be sequenced again if desired. To denature the double stranded PCR template to produce single stranded DNA (ssDNA) for sequencing, the immobilized templates are treated with 0.1N NaOH at room temperature in a flowing stream to remove complementary templates. After washing the reaction capillary and immobilized ssDNA's with buffer, the sequencing primer is introduced into the reaction capillary and annealed to the template in TRIS-HCl, $MgCl_2$, NaCl, and bovine serum albumin ("BSA") and heated to 65° C., followed by cooling to room temperature, and the subsequent addition of an appropriate polymerase enzyme, deoxynucleotide triphosphates ("dNTP's"), and dye-labeled ddNTP's. After primer extension, the excess ddNTP's and dNTP's are removed by washing with buffer. The purified extension products are removed from the wall-immobilized templates by denaturing with mild aqueous alkali. Once the extension products have been removed, the biotinylated template is ready for "resequencing" if desired: another round of treatment with primer, dNTP's, ddNTP's, etc. This procedure can be repeated about six times with little loss of the immobilized templates.

Reagent Flow. The flow of the various reagents through the network of capillaries is preferably controlled either by vacuum pumping or by electrodynamic pumping. For vacuum pumping, one end of a small section of capillary (vacuum tube) is inserted into one arm of a capillary interlock T connector, and the other end of the vacuum tube capillary is connected to a vacuum pump. The other two arms of the interlock T connector are attached to the reaction capillary and to the sample insertion channel of the microcapillary electrophoresis device. The opposite end of the reaction capillary is held stationary, and microtiter dishes with appropriate washing and sequencing reagents are placed on computer-controlled actuators, such as an XYZ-translational stage, to bring appropriate solutions to the reaction capillary network when needed. The capillary tips are positioned in a fixed pattern, matching the geometry of the microtiter dishes.

The pressure drop ($\Delta P$) needed to force solutions through the narrow capillaries can be determined from the length (L) and radius (R) of the capillary, the required volumetric flow rate Q, and the viscosity of the solution $\eta$ from the expression:

$$\Delta P = (8LQ\eta)/(\pi R^4)$$

If the dimensions of the reaction capillary and vacuum capillaries are each given by L=10 cm and R=25 $\mu$m, if $\eta$=1.2 cP, and if Q=100 nL/min (corresponding to a filling time of about 1–2 mins), then the required pressure drop is only about 0.25 atm. This small pressure difference may easily be generated by a small diaphragm pump. The vacuum capillary is sealed in a solution-free vessel using swage fittings and ferrules. A vessel is constructed to accommodate all vacuum lines to the reaction capillaries.

As an alternative one could use electrodynamic pumping, in which an electric field is applied between one end of the reaction capillary and the vacuum capillary. One of the main advantages of electrodynamic pumping is that the linear velocity (and therefore the residence time in the reaction capillary) can be carefully controlled by altering the field strength. To insure that all components move in the same direction, irrespective of their charge, the magnitude of the electroosmotic flow must be somewhat greater than the electrophoretic mobility of each component in the capillary. Because the capillary surface is covered with 3-ATPS, the negative silanol groups of $SiO_2$ have been replaced with positive charges, and therefore the direction of electroosmotic flow is reversed. The electroosmotic flow in a capillary tube coated with 3-ATPS has been measured as $1.55 \times 10^{-4}$ cm$^2$/Vs. (See L. Amankwa et al., "Trypsin-Modified Fused-Silica Capillary Microreactor for Peptide Mapping by Capillary Zone Electrophoresis," *Anal. Chem.*, vol. 64, pp. 1610–1613 (1992).) Because the oligonucleotides, dNTP's, proteins (if solution pH>pI), and ddNTP's each possess an electrophoretic mobility in the same effective direction as that of the reverse-electroosmotic flow, electrodynamic pumping would effectively pump these reagents across the reaction capillary when the injection end (source) is the cathode and the vacuum end is the anode.

A potential concern in applying an electric field to a reaction capillary is the effect that the field might have on the integrity of the biotin/avidin/biotin complex. Any such effect, which is expected to be small, can be measured by radiolabeling the immobilized DNA's with $^{32}$P, and monitoring the activity of the reaction capillary as a function of field strength for various intervals of time and different flow conditions.

Optimizing Reaction Parameters. It is important that the amount of DNA immobilized in the reaction capillary be such that the resulting concentration of extension products is within the detection limits of the detector used. Assuming that the amount of bound DNA is limited by the amount of avidin (whose molecular cross sectional area is about 2000 Å$^2$), and that the capillary surface is saturated with avidin, then the amount of immobilized DNA in a 10 cm long column with a radius of 25 $\mu$m is about $2.6 \times 10^{-12}$ moles. For a capillary volume of 200 nL, this number corresponds to a concentration of approximately 13.3 $\mu$M. If approximately 450 fragments are produced per extension reaction, the concentration of each terminated oligonucleotide would be about $2.7 \times 10^{-8}$M. If the reaction capillary radius is reduced to 12.5 $\mu$m, the Sanger-terminated oligonucleotide concentration increases to about $5.4 \times 10^{-8}$M. If the injection volume for the microcapillary electrophoresis ("CE") device is about 18 pL, then the amount of each extension fragment injected into the CE column would be about $4.8 \times 10^{-19}$ moles (or $9.6 \times 10^{-19}$ moles for a 12.5 $\mu$m column radius), within the mass detection limits for on-column NIR fluorescence—which with current technology is on the order of $3 \times 10^{-20}$ mole with a signal-to-noise ratio of 3.

One way to increase the surface concentration of the oligonucleotides in the reaction capillary, and thus the injection concentration of oligonucleotides to the micro-CE device, is to etch the surface of the reaction capillary to increase its surface area, for example with an HF treatment on a fused-silica capillary increasing the surface area. See, e.g., W. Nashabeh et al., "Enzymorphoresis of Nucleic Acids by Tandem Capillary Enzyme Reactor-Capillary Zone Electrophoresis," *J. Chromatogr.*, vol. 596, pp. 251 ff (1992).

To increase throughput by reducing the number of DNA immobilization cycles needed to sequence a given length of DNA, it is preferred to immobilize 1–40 kb DNA segments, and to use directed methods to sequence these clones. For example, ordered sets of cloned cosmid inserts (40 kb each) would be immobilized onto the reaction capillary surface, significantly reducing the amount of subcloning required. (About 100,000 40 kb cosmids would be required for complete coverage of the human genome).

An upper limit on the size of the immobilized DNA is determined by whether the force exerted on the template under flow conditions will cause shearing. This force is determined partly by the linear flow velocity of the bulk solution. However, the force exerted on the DNA by bulk solvent flow is minimal, because the DNA is immobilized on the surface, and in the case of Poiseuille flow (a parabolic flow profile), the linear velocity near the surface is small. The maximum length of DNA that can be immobilized before shearing effects become deleterious may readily be determined. Different length DNA markers, such as restriction fragments or $\lambda$-phage DNA (48 kbp) are biotinylated using 5'→3' overhangs and standard polymerase enzymes, with a biotinylated ddNTP containing an appropriate-length linker. Immobilizing these DNA's and radiolabeling them with $^{32}$P allows the activity of the column to be monitored as a function of different flow conditions with different lengths of DNA.

Another parameter that may readily be determined is the number of successive sequencing rounds to which an immobilized template may be subjected before there is a substantial loss of signal. This measurement may be made by immobilizing the biotinylated PCR template and subjecting the denatured single strands to multiple rounds of sequencing. By monitoring the steady-state fluorescence signal of the sequencing fragments as a function of the number of sequence rounds, one may readily determine when a reaction capillary should be replenished with additional DNA template under a given set of conditions.

On the last point, it is desirable to remove all bound DNA to eliminate contamination in subsequent rounds of sequencing, but without significantly perturbing covalently-bound biotin. The efficiency of immobilization and the efficiency of removal of the template after sequence analysis can both be determined with an oligonucleotide probe with a $^{32}$P label. After immobilization, the total activity of the capillary can be measured and monitored during several washing, heating, and cooling cycles. Complete removal of the oligonucleotide can be determined by measuring the activity of the capillary after phenol or formamide treatment.

Preparation of a prototype biotinylated template. A prototype template that has been tested was a 900 bp PCK olfaction gene from Ictaluria catfish. The gene was ligated into a pCR II (3.9 kb) vector that had been cleaved with EcoR1 restriction enzyme. The construct was then PCR-amplified for 25 cycles with a T7 primer and a biotinylated SP6 primer. The amplified, biotinylated oligonucleotide product was purified by agarose gel electrophoresis.

Immobilization of the biotinylated template. A 10 cm section of the capillary tube was rinsed with NaOH followed by deionized water, was then purged with air and nitrogen, and was finally oven-baked for 30 min at 80° C. to remove any residual water. The capillary was then filled with a 4% solution of 3-ATPS and incubated for 24 hours at 45° C. The capillary microreactor was then evacuated and filled with a bicarbonate buffer (pH=8.3) containing NHS-LC-biotin for 5 hr at room temperature, to link biotin to the capillary wall. Following biotinylation, the capillary was rinsed with deionized water, and was reacted with a 4.0 mg/mL solution of avidin in 50 mM phosphate buffer (pH=7.3) for 24 hr using gravity flow at a rate of 28 nL/min. The biotinylated DNA template from the previous step was immobilized by filling this capillary with a 1 $\mu$M solution of the PCR amplification products, and allowing it to incubate at 4° C. for 30 min.

Efficiency of immobilization. The amount of immobilized DNA was measured by scintillation counting. The immobilized DNA was labeled with $^{32}$P using T4 polynucleotide kinase. Assuming that the limiting factor is the surface coverage by avidin (whose molecular cross-sectional area is about 20 nm$^2$), then the total amount of DNA that can be immobilized (assuming only one DNA template per avidin molecule and surface saturation) is 1.3 pmols. Using the known activity of the $^{32}$P radiolabel, and the known efficiency of labeling using T4 polynucleotide kinase, the expected activity would be 20,215 cpm. We inserted the entire 10 cm capillary tube directly into the scintillation vial and found a counting rate of 17,500 cpm, corresponding to an immobilization efficiency of about 86%.

Long-term stability of the immobilized DNA. To assess the stability of the biotin:avidin:biotin linkage, we monitored the activity of the microreactor column by scintillation counting daily for two weeks. During the entire two week period, a constant gravity-induced 28 nL/min flow of buffer (1X TBE) passed over the immobilized DNA. After accounting for the half-life of the $^{32}$P label, surface coverage dropped to about 50% of the original amount after 6 days, and to about 32% after 12 days. Similar results were obtained following electrodynamic pumping.

At the end of the 12 day period, additional biotinylated DNA was immobilized in the capillary in essentially the same manner: avidin molecules were inserted into the column first, followed by the biotinylated-DNA template. Total surface coverage was again about 85%, demonstrating that the covalently-immobilized biotin molecule remained intact in the capillary during this extended period of time, and that the microreactor can readily be rejuvenated for additional analyses. After three cycles of immobilizing biotinylated-DNA, there was minimal loss in total surface coverage, showing that the novel microreactor can be re-used for several sequencing runs without replacement.

Temperature stability of immobilized DNA. It is important that the immobilized DNA remain stable over a range of temperatures, because preparing the sequencing ladders requires temperature cycling from room temperature to 85° C. To demonstrate this temperature stability, the microreactor capillary was heated to 65° C. for 2 min (corresponding to primer annealing), cooled over 30 min to 20° C., heated to 37° C. and held for 10 min (corresponding to chain extension), heated to 85° C. and cooled quickly to room temperature (corresponding to denaturing double-stranded DNA). The temperature of the column was regulated by placing the capillary tube in a piece of tygon tubing, and running water at the appropriate temperature through the tubing. There was only a slight loss in surface coverage after ten such temperature cycles. The coverage dropped from 85% initially to approximately 74% after ten temperature cycles performed over a 24-hour period.

These results demonstrate that double-stranded DNA templates can be immobilized with high efficiency, and that the integrity of the immobilized templates remains intact for extended periods of time, and during multiple heating/cooling cycles. In addition, the column can readily be reactivated for subsequent sequencing rounds.

Microfabticated CE Device

An embodiment of a micro-capillary electrophoresis ("micro-CE") system in accordance with the present invention is illustrated in FIG. 1(a)–(d). The micro-CE system is preferably constructed as a microdevice, for example on a poly (methyl methacrylate) ("PMMA") surface. The chip preferably includes two separation channels for redundancy. Because column failure occurs with some frequency but with apparent randomness, placing two separation channels on a single chip allows the system to continue operating until the faulty device is replaced.

A method that has previously been used to introduce samples onto other micro-CE systems has been to seal micropipet tips filled with sample onto the micro-CE chip, and then to use an injection "T" that can be electrically switched to inject sample directly onto the separation column. A drawback of this arrangement is that such a device can be used for only one sample. By contrast, the device depicted in FIG. 1(a) allows multiple reuses, while maintaining the advantages of conventional capillary tubes for sample introduction and maintaining the high speed separations that are possible with micro-CE. In the embodiment depicted in FIG. 1(a) the capillary tubes are sealed to the plate or chip using commercially-available capillary interlock devices bonded to the micro-CE system. The array of flexible capillary tubes is positioned to allow convenient robotic manipulation. The connections also readily allow the micro-CE device to be thoroughly washed with buffer solution prior to reusing the device for subsequent DNA samples.

In FIG. 1(a), PCR templates are placed in reservoirs 2 (microtiter wells), and sample is drawn into reaction capillary 4 by vacuum source 5. Once the sequencing ladders are purified and removed from the surface, the sample is inserted into injection capillary 6, filling injection T 8. The sample is then injected directly onto separation column 10, and oligonucleotides are electrophoretically separated by size by applying an electric field between points 12 and 14. Point 13 provides an electrical ground for the capillary electrophoresis device. FIG. 1(b) depicts a cross-sectional view of the on-chip detection region, showing the preferred mutual orthogonality of column 10, excitation fiber 16, and collection fiber 18. FIGS. 1(c) and 1(d) depict an expanded view of injection T 8, showing first the loading and then the electrokinetic injection of a DNA sample plug 20.

Once injection capillary 6 is filled with sample, which in turn fills injection T 8, the sample is injected into separation column 10 by a voltage applied between points 12 and 14. If the channels at the T junction are 30 µm wide and 20 µm deep, then the injection volume is approximately 18 pL, corresponding to about $4.8 \times 10^{-19}$ moles of each extension product.

It is desirable to use a given CE device repeatedly for many electrophoretic runs. Such repeated use requires that the electrophoresis sieving matrix be replaced after each run. Examples of suitable sieving matrices are polyacrylamide and polyethylene oxide (PEO) in an uncoated capillary column. E. Fung et al., "High-Speed DNA Sequencing by Using Mixed Poly(ethylene oxide) Solutions in Uncoated Capillary Columns," *Anal. Chem.*, vol. 67, pp. 1913–1919 (1995) demonstrated that mixed PEO solutions with denaturing agents can produce separations comparable to those for LPA matrices. Read lengths up to 420 bases were achieved with electrophoresis development times of 16 minutes in a 35 cm uncoated capillary. The fast development time resulted from the relatively low viscosity of this polymer mixture (1200 cP). However, the wall had to be reconditioned after each run with 0.1N HCl. Pumping a 1200 cP PEO polymer through a 30 µm diameter, 20 cm long capillary at a flow rate of 25 nL/min (i.e., a filling time of 5 min) would require a pressure drop of about 49 atm.

Filling and emptying the separation column for reconditioning can be accomplished via conventional fused silica capillaries attached to the ends of the microchannel etched in the microchip. The capillary tips may be placed into a high pressure vessel filled with a regenerating gel solution. After the column has been regenerated, the capillary tips can be placed in the buffer reservoirs, and an electric field can then be applied across the separation column to inject the DNA plug and start a separation. The capillary tips of the array are held stationary, and the pressure vessels and buffer reservoirs are placed on a computer-controlled platform such as an XYZ-translational stage to automate the micro-CE conditioning and electrophoresis steps.

Among the difficulties of a system etched onto glass are the following: (1) The charged surface of glass can degrade the separating ability of the system, a problem that has been addressed in the past by applying a polymeric coating to the glass to minimize surface charges. But under an electric field such a polymeric coating degrades, eventually rendering the device useless. (2) The wet etching process is isotropic, and therefore produces channels that are shallow and wide, i.e., that have a low aspect ratio. In addition, this type of wet etching prevents micro-machining three-dimensional structures such as optical components onto the same device. (3) The sample is introduced into the device using a micro-pipet tip that is sealed to the glass substrate and filled with sample. Therefore, the device can be used for only one sample, and then must be discarded.

A novel and preferred approach to solve these problems is to use an x-ray-sensitive polymer without substantial surface charge, directly as the substrate for forming CE microchannels instead of using glass. The primary advantage of this approach is that resists without a surface charge require no extrinsic polymeric coating, greatly extending the lifetime of the micro-fabricated device. Examples of such x-resists (many of which are also e-beam resists) are polyacrylates, poly (olefin sulfones), poly (diene sulfones), and epoxy resists. An example of a polyacrylate is poly (methyl methacrylate) ("PMMA"). An example of a poly (olefin sulfone) is poly (butene-1-sulfone) ("PBS"). An example of a poly (diene sulfone) is poly (1,3-hexadiene sulfone) ("PHS"). An example of an epoxy resist is "COP", a copolymer of glycidyl methacrylate and ethyl acrylate. Such compounds are disclosed, for example, L. Thompson et al. (eds.), *Introduction to Microlithography*, pp. 198–267 (2nd ed. 1994); and in commonly-assigned U.S. patent application Ser. No. 08/567,654, filed Dec. 5, 1995.

Microfabrication on an x-ray-sensitive polymer without substantial surface charge allows the production of deep channels with narrow widths, i.e., with high aspect ratios. Not only are device lifetimes extended, but the use of high aspect ratio microchannels itself results in more predictable flow. In addition, three-dimensional structures such as optical components may be machined directly onto the device as desired. Preferred lithographic techniques for manufacturing high aspect ratio microdevices are disclosed in Y. Vladimirsky et al., "Microstructures and Methods for Manufacturing Microstructures," international patent application serial number PCT/US94/10164, filed 9 Sep. 1994, published as WO 96/07954 on 14 Mar. 1996.

Figure 2:
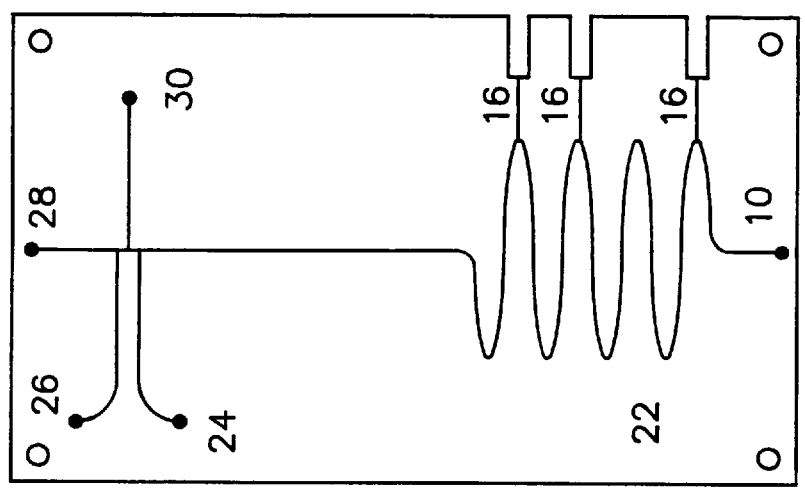
FIG. 2 depicts a micro-capillary electrophoresis device in accordance with the present invention.

FIG. 2 illustrates a micro-capillary electrophoresis device in accordance with the present invention, prepared using these high-aspect ratio techniques on PMMA. Capillary 10 on PMMA substrate 22 is adapted to hold the gel. Injector ports 24, 26, 28, and 30, without any gel, are adapted to inject different sample plug sizes. Optic fibers 16 are positioned to allow a reasonable column length for high resolution; a preferred distance is about 9 cm from injection. These fibers 16 transmit excitation light to column 10. Collection fibers 18 (not shown in FIG. 2), positioned at 90° to both excitation fiber 16 and to the direction of electrophoretic flow through column 10, collect fluorescence emission photons for delivery to a detector (not illustrated).

Using known techniques in micromachining and photolithography, the excitation laser and the diode detector are preferably machined directly onto the same device containing the micro capillary electrophoresis column.

To multiplex the device and to permit automated electrokinetic injection, individual microchips with two separation lanes each will be configured into an array. The fused-silica capillaries are permanently mounted in an array whose dimensions match the inter-well spacing of a microtiter dish. The front section of tubing is the reaction capillary, and is connected to a T-shaped capillary interlock. Another arm of the T connects to the injection capillary, and the third arm to the vacuum capillary. After the sequencing ladders have been purified in the reaction capillary and denatured from the immobilized template, they are inserted into the CE system by applying a voltage or pressure between points 12 and 14 (see FIG. 1(*a*)). Because point 2 is actually a well of the microtiter dish, an electrode is inserted into this well.

For example, 96-well plates are constructed by inserting a small Pt wire into each well of the microtiter dish and allowing it to protrude from the bottom of the plate. A socket electrically connects to each of the microwires protruding from the microtiter dish. A single connection from the microtiter well socket is made to a high voltage power supply.

The number of separation lanes needed to sequence approximately 1–2 million bases of raw data per instrument per day can be estimated, based on the assumption that the rate-limiting step is the development of the electropherogram. The results of this calculation are shown in Table 1. The calculations assume that 10 cm of column will produce sufficient electrophoretic resolution to separate and detect all bases in the reaction products of a given PCR template. Table 1 assumes a column length of 10 cm, and a field strength of 250 V/cm. Note that only 17 lanes are required for a sequencing rate exceeding 1 million bases per day per instrument, demonstrating the remarkable efficiency of the novel system.

TABLE 1

Throughput analysis of CE multiplexed sequencing device using poly (ethylene oxide) sieving matrices.

| | |
|---|---|
| Apparent mobility of a 420-mer | $1.4 \times 10^{-4}$ cm$^2$/Vs |
| Accessible Field Strength | 250 V/cm |
| Gel Matrix Composition | poly(ethylene oxide) |
| Column length (injection to detection) | 10 cm |
| Development Time of Electropherogram | 4.9 min |
| Reconditioning time for Column (see note below) | 5.0 min |
| Number of Bases per day per lane | 61,000 |
| Number of lanes required to sequence $1.0 \times 10^6$ bases per day per instrument | 17 |

Note: With the use of PMMA micro-CE devices, column reconditioning, which is typically performed in glass CE devices, will not be required. Eliminating this step will further increase the speed of the separation process.

The serial design of the present system minimizes "overhead" time. Table 1 includes no allowance for overhead time associated with preparing sequencing ladders, because the system is designed so that sequencing reactions may be run concurrently with electrophoresis, and it is assumed that electrophoresis is the rate-limiting step. While electrophoresis is occurring on one round of sequencing ladders, the next round of sequencing ladders can simultaneously be prepared in the reaction capillary by simply reinserting the appropriate reagents with either vacuum or electrodynamic pumping. If vacuum pumping is used, the pressure drop needed to pump the low-viscosity solutions through the affected portion of the network is sufficiently small (0.25 atm) not to disrupt the ongoing separation process.

Ultrasensitive NIR Detection and Lifetime Measurements

The novel detection system satisfies several criteria:

1. Ultra-high sensitivity. Because the material loaded onto the gel column may contain as few as 1000–10,000 DNA molecules, existing laser detection devices may not be sufficiently sensitive.

2. On-column detection. The ability to detect materials directly on-chip simplifies the detection apparatus. Existing ultrasensitive detection methods, using visible excitation and detection, require off-column detection in a sheath flow cell due to fluorescence attributable to impurities and to photons scattered by the gel matrix.

3. Fluorescence lifetime measurements. The present system dynamically measures fluorescence lifetimes for base-calling with high accuracy and precision, even with the small absolute number of counts obtained from the small amount of material within each electrophoretic band. These lifetimes may be measured using either time-domain techniques or frequency-domain techniques known in the art.

4. Inexpensive and easily operated instrumentation. The device allows easy operation and upkeep, even by users not well trained in lasers and optics. The device has minimal set-up costs.

5. The detection apparatus does not require optical realignment when gel columns are replaced. Gels require periodic replacement due to the loss in separation efficiency resulting from breakdown. The novel device does not require optical realignment when gels are replaced, minimizing down-time.

A device has been constructed that satisfies criteria 1–4 above, using near-infrared ("NIR") excitation from a simple mode-locked diode laser with a single photon avalanche diode as a fast detector, and work is underway on a detection apparatus that will satisfy criterion 5. Because there is such low background noise with NIR excitation and detection, single molecules have been successfully detected in a prototype device. Background noise is low not only because few compounds have intrinsic fluorescence in the near-infrared, but also because Raman contribution to the background is low due to the Raman cross section's $\lambda^{-4}$ dependence.

Fluorescence Detection—Array Detection versus Single Channel Detection

Fluorescence from the migrating oligonucleotide fragments is monitored on chip by point detection. The detector preferably employs a series of two optical fibers, one to deliver excitation light to the chip, and one to collect the fluorescence emission and direct it to signal processing electronics. To maximize resolution and to reduce the total number of optical components, it is preferred that a single optical fiber be used to deliver the excitation light, and a single fiber to collect and transmit the fluorescence emission. Preferably a single fiber delivers the excitation light from a laser, and a single fiber positioned at 90° to the first fiber collects the fluorescence emissions from the sample. Channels are etched into the chip to accommodate the optical fibers, which are sealed to the chip, for example, with epoxy. With the fibers permanently mounted onto the chip, once the chip is constructed no optical realignment is thereafter necessary.

Processing lifetime-resolved fluorescence data to identify terminal bases can be accomplished either with an array detector or with a single channel detector reading data serially. An advantage of a single channel detector is that the photodetector can be less instrumentally intensive and less expensive. However, reading data serially can also degrade the signal-to-noise ratio. The total data sampling rate (integration time per data point) required for 17 lanes, with 10 data points per peak and a peak width of approximately 0.7 s, is about 5 ms. If the electronic transition is near saturation (a condition that optimizes the signal-to-noise ratio, especially for an ultrasensitive measurement), and if the observed molecules (e.g., the NIR chromophores) are bleached before exiting the detection zone, then the fluorescence photon detection rate per molecule is approximately 4.0 (assuming $\Phi_f=0.2$; $\Phi_d=1\times10^{-4}$; absorption rate=$80\times10^6$ (repetition rate of pulsed laser); single photon detection efficiency of instrument (composite of quantum efficiency of detector, geometrical collection efficiency, sampling efficiency of molecules eluting through column, transmission efficiency of the bandpass filter, and time-gate efficiency)=0.002). If each electrophoretic band comprises $4.8\times10^{-19}$ moles of DNA ($2.8\times10^5$ molecules), and assuming a duty cycle of 6% (sequentially reading each of 17 lanes), then the integrated number of photons per band is about 67,000. This photon number is sufficient for effective lifetime measurements. Thus serial reading of 17 different lanes with a single channel detector provides sufficient sensitivity. If greater sensitivity is desired, one may always use an array detector instead, at the cost of increased instrumental complexity and greater expense.

An optical system for collecting and processing the fluorescence signals from the collection fibers is depicted in FIG. 3. For clarity, only three of the collection optical fibers 18 are shown. The terminal ends of the fibers are mounted in a holder placed in front of a microlens array of GRIN (graded refractive index) lenses 32. These microlens arrays are fabricated to collimate light from a point source. After collimation, the light is filtered through spectral filter 34, and then reflected off moving mirror 36 (to selectively collect photons from the different lanes). The reflected light is focused with lens 38 onto the photoactive area of a single photon avalanche diode detector ("SPAD") 40, whose output is transmitted to processing electronics and computer 44. To keep the off-axis rays (light other than from the fiber being sampled) from the photodetector, a pin hole or spatial filter 42 is situated directly in front of the detector.

Single mode fibers have features that are desirable for the present application. The radial distribution of the electric field in a single mode fiber has only one mode, with a nearly Gaussian form. The output of a single mode fiber can be focused to a diffraction-limited spot using a spherical lens, whereas the output of a multimode fiber cannot. Because SPAD detectors have photoactive areas about 150 μm in diameter, and because tight focusing of the radiation on the face of the diode is required for optimal timing response in time-correlated single-photon counting ("TCSPC") applications, the image formed on the diodes should be smaller than the photoactive area of the diode itself. For the novel optical system, the focusing microlens array isf-matched to the collimating lenses, giving a magnification of 1. With collection optical fibers having a core diameter of 5.5 um, the image formed on the face of the array detector should be approximately 10–20 μm, suitable for optimal timing characteristics in SPAD detectors.

Another desirable feature of single mode fibers is that temporal dispersion of pulsed light travelling through the fibers can be orders of magnitude less than is the case for multimode fibers of comparable length. Small temporal dispersions are particularly important, because accurate lifetime measurements require narrow instrument response functions. Wavelength dispersion in a single mode fiber is also minimal, and is generally less than the observed instrument response function produced by transit time spread in the detector.

The single mode fibers used for light delivery and collection have core diameters of only 5.5 μm. This small diameter forces the fiber to support only a single mode. The effective collection efficiency for a small optic can be low. However, the novel system achieves a bigh collection efficiency due to the small distance between the collection optic and the excitation beam. If the capillary channel is 20 μm in diameter, the distance from a point source (emitting molecule) at the center of the capillary channel to the face of the collecting optical fiber is only 10 μm. The effective collection efficiency for this point source is 2%; and the collection efficiency increases to 6% for a capillary channel with a diameter of 10 μm. Thus even though the collection optic has a small effective aperture, its close proximity to the emitting source results in overall collection efficiencies comparable to those of microscope objectives. Another advantage is that any scattering at the interfaces falls outside the field of view of the collection optic, resulting in less background noise. A further advantage is that single mode fibers are relatively inexpensive, costing about $4.00 per meter.

To make the electronics for lifetime-resolved measurements transparent to the user, a constant fraction discriminator, a time-to-amplitude converter (TAC), and a multichannel scaler will be placed on a board inserted directly into a dedicated computer. The board is controlled exclusively by software, which minimizes the overhead associated with optimizing its electronics. Such boards are commercially available, and can be run in a multi-channel format collecting up to 20 decay profiles at a counting rate up to about 6 million counts per second. The multichannel scaler collects and displays normal intensity electropherograms. Decay lifetimes are calculated on-line using existing algorithms suitable for low counting rates.

The laser source for the prototype system has been a mode locked diode laser driven by a picosecond current pulser. This laser produced pulses approximately 200 ps in duration at a repetition rate of 80 MHz. The laser operated in a $TEM_{00}$ axial mode structure, allowing diffraction-limited focusing, and easy coupling into single-mode optical fibers to deliver light to the separation channels. This laser operated at 750 nm, at 7 mW power. The advantages of the diode laser include low cost, low power requirements, and extended lifetimes, with minimal upkeep.

We have constructed a time-correlated single-photon counting ("TCSPC") system using a diode laser operated in pulsed mode to excite fluorescence, a single-photon avalanche diode ("SPAD") detector, and counting electronics on a PC-board. The device demonstrated a time resolution of 250 ps (full width at half-maximum), which allows measurement of lifetimes down to about 300 ps with reasonable accuracy and precision. The laser operated at 80 MHz with an average power of 7 mW at 780 nm.

This instrument was used to measure the fluorescence lifetimes of A- and C-terminated Sanger dideoxynucleotides, using two different near-IR dyes as labels. The dyes have similar absorption and emission spectra, but distinct lifetimes (previously measured as 660 ps and 580 ps). The lifetimes were measured on-line with the TCSPC system during the capillary gel electrophoretic separation of the fragments. The on-line measurement of the fluorescence lifetime for the A-terminated fragment was 575 ps, while that for the C-terminated fragment was 689 ps, demonstrating that this system readily distinguished the two dyes in an on-line measurement. (It was established in earlier experiments that this capillary electrophoresis column has one-base-pair resolution in separating Sanger oligonucleotides.)

The system may be operated in a multiplexed fashion, using single mode optical fibers for light delivery and collection, with no optical alignment or re-optimization required after the system has been constructed. The detection region is built on a micromachined PMMA plate having a series of microchannels photolithographically etched onto the plate using known lithographic techniques.

The construction of a micro-machined fiber optic detection system in accordance with this invention had nearly been completed at the time the present application is being filed. Optic fibers were etched to the appropriate diameter using HF solution. In particular, a single-mode optic fiber was etched for about 6 hours in dilute HF; inspection by scanning electron microscopy demonstrated that the fiber had the desired diameter of 40 μm. A microchannel 50 μm wide was machined in a PMMA substrate using x-ray lithography. The etched fiber was placed on a micro-positioning device, and was inserted into the microchannel using a high-power optical microscope. The fiber was sealed to the PMMA substrate using a small amount of epoxy cement. Coupling the diode laser to this fiber resulted in about 3 mW average laser power being delivered to the micro-CE separation channel. Work is currently underway to insert the collection fiber into the micro-CE system using similar techniques.

The Near-Infrared Dyes

Preferred dyes for use in this system are certain near-infrared ("NIR") dyes. An advantage of using NIR dyes is that detection can be performed directly in the gel column without sacrificing sensitivity, and that there is little background noise at the frequencies of interest. In addition, NIR fluorescence allows the use of simple diode lasers and solid-state photodetectors. Base-calling requires that four DNA bases be distinguished from one another. The preferred dyes are a set of four heavy-atom-modified NIR dyes that have similar absorption and emission maxima but distinct fluorescent lifetimes, permitting the use of a single excitation laser and a single detection channel. These dyes are attached to the ddNTP's that act as chain terminators in preparing Sanger sequencing ladders. The different lifetimes are achieved by incorporating different heavy atoms into the framework of the NIR dye molecule. Base identification is performed by dynamic fluorescent lifetime measurements. An additional advantage is that, unlike an absorption spectrum or even a fluorescence spectrum, a lifetime measurement does not depend on the amount of material being measured. Thus a single-lane, single-fluorophore method can be used to identify bases.

Preferred dyes are the tricarbocyanine dyes disclosed in S. Soper et al., "Micro-DNA Sequence Analysis Using Capillary Electrophoresis and Near-IR Fluorescence Detection," *SPIE*, vol. 2680, pp. 235–246 (proceedings paper, San Jose, Calif., Feb. 2, 1996); and D. Williams et al., "Single-Lane, Single-Fluor Sequencing using Dideoxy-Labeled, Heavy-Atom Modified Near-TR Fluorescent Dyes," *SPIE*, vol. 2386, pp. 55–65 (proceedings paper, presentation in San Jose, Calif., Feb. 6, 1995).

Using an estimated photoelectron yield per molecule, the total number of counts used to construct the decay profile for the lifetime determination of 2000 molecules is about 36,000. If this lifetime is calculated over a time interval in which scattering photons are minimal (for our prototype system with a measured 170 ps FWHM instrument response, such a state occurs 125 ps after excitation), and if it is assumed that the lifetime of the dye-labeled oligonucleotides is 900 ps, then the total number of counts included in the calculation is approximately 32,000. The overall measurement accuracy is therefore about ±0.5%. Assuming that accurate lifetime measurements for definitive identification of the chain terminator require lifetimes that are separated from one another by three standard deviations, then the lifetimes could, for example, be as close together as 900 ps, 887 ps, 874 ps, and 861 ps. Only small incremental changes in the lifetimes are needed when the total number of photoelectron counts in the decay profile is high. If the number of detected molecules were increased, then the lifetimes could be even closer to one another, and still permit definitive identification.

An important feature of measuring lifetimes rather than frequencies to discriminate among bases is that the measured value is immune to variations in signal intensity that can result from non-uniform incorporation of the various ddNTP's by the polymerase. Thus this system is suitable for a single lane, single fluorophore approach, with the ability to select from different polymerase enzymes for particular applications.

The complete disclosures of all references cited in this specification are hereby incorporated by reference. In the event of an otherwise irreconcilable conflict, however, the present specification shall control.

We claim:

1. A method for sequencing DNA, comprising the sequential steps of:

(a) covalently linking the DNA to a first compound;

(b) transferring the DNA into a capillary having a volume less than about 1 $\mu$L, wherein a second compound is bound to the inner wall of the capillary, wherein the first compound binds to the second compound with high affinity, whereby the DNA becomes immobilized on the inner wall of the capillary;

(c) synthesizing oligonucleotides complementary to all or a portion of the immobilized DNA with a DNA polymerase and DNA primers; wherein the oligonucleotides are substantially identical to one another, except that the 3' ends of the oligonucleotides are a variable distance from a common 5' end, so that the oligonucleotides have variable lengths; wherein the terminal nucleotide base on the 3' end of the oligonucleotides is linked to one of four labels that is spectroscopically detectable, and that identifies the nucleotide base to which it is linked; and wherein the oligonucleotides are synthesized within the capillary containing the immobilized DNA;

(d) transferring the oligonucleotides to a microfabricated capillary electrophoresis column, and electrophoretically separating the oligonucleotides within the column by size; and (e) spectroscopically detecting and identifying the labels linked to the electrophoretically separated oligonucleotides;

whereby the order in which the labels of the electrophoresed oligonucleotides are detected corresponds to the sequence of at least a portion of the DNA.

2. A method as recited in claim 1, wherein the first compound comprises biotin, and wherein the second compound comprises biotin that is bound to the inner wall of the capillary and that is also bound to avidin or streptavidin.

3. A method as recited in claim 2, wherein the method is repeated to sequence new DNA after the original DNA is sequenced; and wherein between the two repetitions of the method the following sequential steps occur:

(a) removing the original DNA from the capillary by denaturing the avidin or streptavidin without denaturing the biotin, and then flushing the original DNA and denatured avidin or streptavidin from the capillary; whereby biotin remains bound to the inner wall of the capillary; and (b) transferring new avidin or streptavidin into the capillary, whereby the avidin or streptavidin binds to the biotin on the inner wall of the capillary, whereby the capillary is regenerated to be able to bind new DNA linked to biotin.

4. A method as recited in claim 1, wherein the first compound comprises an antigen, and wherein the second compound comprises a monoclonal antibody that specifically binds the antigen.

5. A method as recited in claim 1, wherein the capillary in which the DNA is immobilized has a volume less than about 200 nanoliters.

6. A method as recited in claim 1, wherein said synthesizing step comprises synthesizing oligonucleotides whose variable end comprises labelled dideoxynucleotides.

7. A method as recited in claim 1, wherein said spectroscopic detecting and identifying step comprises measuring near-infrared laser-induced fluorescence of the labels.

8. A method as recited in claim 7, wherein the four labels that identify the nucleotide bases are each near-infrared fluorophores; wherein the near-infrared absorption maxima of each of the four fluorophores are similar; wherein the near-infrared fluorescence maxima of each of the four fluorophores are similar; wherein the fluorescence lifetimes of each of the four fluorophores are different; and wherein the labels linked to the electrophoretically separated oligonucleotides are identified by measuring the fluorescence lifetimes of the labels.

9. A method as recited in claim 7, wherein said spectroscopic detecting and identifying step comprises transmitting near-infrared laser light through a first single-mode optic fiber to excite the labels of the electrophoretically separated oligonucleotides; and collecting near-infrared fluorescent photons from the labels with a second single-mode optic fibers; wherein the two optic fibers are positioned at approximately 90° relative to one another; and wherein each of the two optic fibers is positioned at approximately 90° relative to the direction of electrophoretic travel of the oligonucleotides.

10. A method as recited in claim 1, wherein the rate of DNA sequencing of said method is at least about 20 bases per capillary electrophoresis column per minute.

11. A method as recited in claim 1, wherein the capillary electrophoresis column is fabricated in an x-ray resist substrate, wherein the x-ray resist has no substantial surface charge.

12. A method as recited in claim 11, wherein the x-ray resist comprises a polyacrylate.

13. A method as recited in claim 12, wherein the x-ray resist comprises poly(methyl methacrylate).

14. A method as recited in claim 11, wherein the x-ray resist comprises a poly(diene sulfone).

15. A method as recited in claim 14, wherein the x-ray resist comprises poly(1,3-hexadiene sulfone).

16. A method as recited in claim 11, wherein the x-ray resist comprises a poly(olefin sulfone).

17. A method as recited in claim 16, wherein the x-ray resist comprises poly(butene-1-sulfone).

18. A method as recited in claim 11, wherein the x-ray resist comprises an epoxy resist.

19. A method as recited in claim 18, wherein the x-ray resist comprises a copolymer of glycidyl methacrylate and ethyl acrylate.

20. An apparatus for sequencing DNA, using first and second compounds that bind to one another with high affinity, said apparatus comprising:
(a) a capillary having a volume less than about 200 nanoliters, wherein the inner wall of said capillary binds or is capable of binding the second compound, and wherein said capillary is adapted to immobilize DNA that is linked to the first compound by allowing the first and second compounds to bind to one another, whereby the DNA becomes immobilized on the inner wall of said capillary; wherein said capillary is capable of acting as a reaction vessel for synthesizing, within said capillary, oligonucleotides complementary to all or a portion of the immobilized DNA with a DNA polymerase and DNA primers; wherein the oligonucleotides are substantially identical to one another, except that the 3' ends of the oligonucleotides are a variable distance from a common 5' end, so that the oligonucleotides have variable lengths; and wherein the terminal nucleotide base on the 3' end of the oligonucleotides is linked to a label that is spectroscopically detectable, and that identifies the nucleotide base to which it is linked;
(b) a microfabricated capillary electrophoresis column connected to said capillary to receive the synthesized oligonucleotides, and to electrophoretically separate the oligonucleotides within the column by size; and
(c) a detector to spectroscopically detect and identify the labels linked to the electrophoretically separated oligonucleotides;
whereby the order in which the labels of the electrophoresed oligonucleotides are detected corresponds to the sequence of at least a portion of the DNA.

21. An apparatus for sequencing DNA, using first and second compounds that bind to one another with high affinity, said apparatus comprising:
(a) a capillary having a volume less than about 1 $\mu$L, wherein the inner wall of said capillary binds or is capable of binding the second compound, and wherein said capillary is adapted to immobilize DNA that is linked to the first compound by allowing the first and second compounds to bind to one another, whereby the DNA becomes immobilized on the inner wall of said capillary; wherein said capillary is capable of acting as a reaction vessel for synthesizing, within said capillary, oligonucleotides complementary to all or a portion of the immobilized DNA with a DNA polymerase and DNA primers; wherein the oligonucleotides are substantially identical to one another, except that the 3' ends of the oligonucleotides are a variable distance from a common 5' end, so that the oligonucleotides have variable lengths; and wherein the terminal nucleotide base on the 3' end of the oligonucleotides is linked to a label that is spectroscopically detectable, and that identifies the nucleotide base to which it is linked;
(b) a microfabricated capillary electrophoresis column connected to said capillary to receive the synthesized oligonucleotides, and to electrophoretically separate the oligonucleotides within the column by size; and
(c) a detector to spectroscopically detect and identify the labels linked to the electrophoretically separated oligonucleotides; wherein said detector comprises a first single-mode optic fiber to transmit near-infrared laser light through the electrophoretically separated oligonucleotides to excite the labels of the electrophoretically separated oligonucleotides; and a second single-mode optic fiber to collect near-infrared fluorescent photons from the labels on the electrophoretically separated oligonucleotides; wherein the two said optic fibers are positioned at approximately 90° relative to one another; and wherein each of the two said optic fibers is positioned at approximately 90° relative to the direction of electrophoretic travel of the oligonucleotides;
whereby the order in which the labels of the electrophoresed oligonucleotides are detected corresponds to the sequence of at least a portion of the DNA.

22. An apparatus for sequencing DNA, using first and second compounds that bind to one another with high affinity, said apparatus comprising:
(a) a capillary having a volume less than about 1 $\mu$L, wherein the inner wall of said capillary binds or is capable of binding the second compound, and wherein said capillary is adapted to immobilize DNA that is linked to the first compound by allowing the first and second compounds to bind to one another, whereby the DNA becomes immobilized on the inner wall of said capillary; wherein said capillary is capable of acting as a reaction vessel for synthesizing, within said capillary, oligonucleotides complementary to all or a portion of the immobilized DNA with a DNA polymerase and DNA primers; wherein the oligonucleotides are substantially identical to one another, except that the 3' ends of the oligonucleotides are a variable distance from a common 5' end, so that the oligonucleotides have variable lengths; and wherein the terminal nucleotide base on the 3' end of the oligonucleotides is linked to a label that is spectroscopically detectable, and that identifies the nucleotide base to which it is linked;
(b) a microfabricated capillary electrophoresis column connected to said capillary to receive the synthesized oligonucleotides, and to electrophoretically separate the oligonucleotides within the column by size, wherein said capillary electrophoresis column is fabricated in an x-ray resist substrate, wherein the x-ray resist has no substantial surface charge, and wherein the x-ray resist comprises a polyacrylate; and (c) a detector to spectroscopically detect and identify the labels linked to the electrophoretically separated oligonucleotides;

whereby the order in which the labels of the electrophoresed oligonucleotides are detected corresponds to the sequence of at least a portion of the DNA.

23. An apparatus as recited in claim 22, wherein the x-ray resist comprises poly(methyl methacrylate).

24. An apparatus for sequencing DNA, using first and second compounds that bind to one another with high affinity, said apparatus comprising:

(a) a capillary having a volume less than about 1 $\mu$L, wherein the inner wall of said capillary binds or is capable of binding the second compound, and wherein said capillary is adapted to immobilize DNA that is linked to the first compound by allowing the first and second compounds to bind to one another, whereby the DNA becomes immobilized on the inner wall of said capillary; wherein said capillary is capable of acting as a reaction vessel for synthesizing, within said capillary, oligonucleotides complementary to all or a portion of the immobilized DNA with a DNA polymerase and DNA primers; wherein the oligonucleotides are substantially identical to one another, except that the 3' ends of the oligonucleotides are a variable distance from a common 5' end, so that the oligonucleotides have variable lengths; and wherein the terminal nucleotide base on the 3' end of the oligonucleotides is linked to a label that is spectroscopically detectable, and that identifies the nucleotide base to which it is linked;

(b) a microfabricated capillary electrophoresis column connected to said capillary to receive the synthesized oligonucleotides, and to electrophoretically separate the oligonucleotides within the column by size, wherein said capillary electrophoresis column is fabricated in an x-ray resist substrate, wherein the x-ray resist has no substantial surface charge, and wherein the x-ray resist comprises a poly(diene sulfone); and (c) a detector to spectroscopically detect and identify the labels linked to the electrophoretically separated oligonucleotides;

whereby the order in which the labels of the electrophoresed oligonucleotides are detected corresponds to the sequence of at least a portion of the DNA.

25. An apparatus as recited in claim 24, wherein the x-ray resist comprises poly(1,3-hexadiene sulfone).

26. An apparatus for sequencing DNA, using first and second compounds that bind to one another with high affinity, said apparatus comprising:

(a) a capillary having a volume less than about 1 $\mu$L, wherein the inner wall of said capillary binds or is capable of binding the second compound, and wherein said capillary is adapted to immobilize DNA that is linked to the first compound by allowing the first and second compounds to bind to one another, whereby the DNA becomes immobilized on the inner wall of said capillary; wherein said capillary is capable of acting as a reaction vessel for synthesizing, within said capillary, oligonucleotides complementary to all or a portion of the immobilized DNA with a DNA polymerase and DNA primers; wherein the oligonucleotides are substantially identical to one another, except that the 3' ends of the oligonucleotides are a variable distance from a common 5' end, so that the oligonucleotides have variable lengths; and wherein the terminal nucleotide base on the 3' end of the oligonucleotides is linked to a label that is spectroscopically detectable, and that identifies the nucleotide base to which it is linked;

(b) a microfabricated capillary electrophoresis column connected to said capillary to receive the synthesized oligonucleotides, and to electrophoretically separate the oligonucleotides within the column by size, wherein said capillary electrophoresis column is fabricated in an x-ray resist substrate, wherein the x-ray resist has no substantial surface charge, and wherein the x-ray resist comprises poly(butene-1-sulfone); and (c) a detector to spectroscopically detect and identify the labels linked to the electrophoretically separated oligonucleotides;

whereby the order in which the labels of the electrophoresed oligonucleotides are detected corresponds to the sequence of at least a portion of the DNA.

27. An apparatus for sequencing DNA, using first and second compounds that bind to one another with high affinity, said apparatus comprising:

(a) a capillary having a volume less than about 1 $\mu$L, wherein the inner wall of said capillary binds or is capable of binding the second compound, and wherein said capillary is adapted to immobilize DNA that is linked to the first compound by allowing the first and second compounds to bind to one another, whereby the DNA becomes immobilized on the inner wall of said capillary; wherein said capillary is capable of acting as a reaction vessel for synthesizing, within said capillary, oligonucleotides complementary to all or a portion of the immobilized DNA with a DNA polymerase and DNA primers; wherein the oligonucleotides are substantially identical to one another, except that the 3' ends of the oligonucleotides are a variable distance from a common 5' end, so that the oligonucleotides have variable lengths; and wherein the terminal nucleotide base on the 3' end of the oligonucleotides is linked to a label that is spectroscopically detectable, and that identifies the nucleotide base to which it is linked;

(b) a microfabricated capillary electrophoresis column connected to said capillary to receive the synthesized oligonucleotides, and to electrophoretically separate the oligonucleotides within the column by size, wherein said capillary electrophoresis column is fabricated in an x-ray resist substrate, wherein the x-ray resist has no substantial surface charge, and wherein the x-ray resist comprises an epoxy resist; and (c) a detector to spectroscopically detect and identify the labels linked to the electrophoretically separated oligonucleotides;

whereby the order in which the labels of the electrophoresed oligonucleotides are detected corresponds to the sequence of at least a portion of the DNA.

28. An apparatus as recited in claim 27, wherein the x-ray resist comprises a copolymer of glycidyl methacrylate and ethyl acrylate.

29. A capillary electrophoresis column microfabricated in an x-ray resist substrate, wherein the x-ray resist has no substantial surface charge, and wherein the x-ray resist comprises a polyacrylate.

30. A capillary electrophoresis column as recited in claim 29, wherein the x-ray resist comprises poly(methyl methacrylate).

31. A capillary electrophoresis column microfabricated in an x-ray resist substrate, wherein the x-ray resist has no substantial surface charge, and wherein the x-ray resist comprises a poly(diene sulfone).

32. A capillary electrophoresis column as recited in claim 31, wherein the x-ray resist comprises poly(1,3-hexadiene sulfone).

33. A capillary electrophoresis column microfabricated in an x-ray resist substrate, wherein the x-ray resist has no substantial surface charge, and wherein the x-ray resist comprises poly(butene-1-sulfone).

34. A capillary electrophoresis column microfabricated in an x-ray resist substrate, wherein the x-ray resist has no substantial surface charge, and wherein the x-ray resist comprises an epoxy resist.

35. A capillary electrophoresis column as recited in claim 34, wherein the x-ray resist comprises a copolymer of glycidyl methacrylate and ethyl acrylate.

36. A capillary micro-electrophoresis column comprising an integrated optical system for detecting a fluorescent component of a sample in said column, said integrated optical system comprising a first single mode optic fiber for delivering laser excitation light to the sample in said column, and a second single mode optic fiber for collecting fluorescent photons from the sample in said column and delivering the fluorescent photons to a detector, wherein said first and second optic fibers are positioned at approximately 90° relative to one another.

37. A capillary electrophoresis column as recited in claim 36, additionally comprising a diode laser integrated into said optical system, wherein said diode laser is positioned to deliver excitation light to said first optic fiber.

38. A capillary electrophoresis column as recited in claim 36, additionally comprising a detector integrated into said optical system, wherein said detector is positioned to receive and detect fluorescence photons from said second optic fiber.

39. A capillary electrophoresis column as recited in claim 38, additionally comprising a diode laser integrated into said optical system, wherein said diode laser is positioned to deliver excitation light to said first optic fiber.

* * * * *